United States Patent
Ramsay et al.

(10) Patent No.: US 9,754,078 B2
(45) Date of Patent: Sep. 5, 2017

(54) HAPTIC HEALTH FEEDBACK MONITORING

(75) Inventors: Erin B. Ramsay, Montreal (CA); Robert W. Heubel, San Leandro, CA (US); Neil Thomas Olien, Montreal (CA)

(73) Assignee: Immersion Corporation, San Jose, CA (US)

( * ) Notice: Subject to any disclaimer, the term of this patent is extended or adjusted under 35 U.S.C. 154(b) by 481 days.

(21) Appl. No.: 11/766,452

(22) Filed: Jun. 21, 2007

(65) Prior Publication Data

US 2008/0319279 A1    Dec. 25, 2008

(51) Int. Cl.
| | |
|---|---|
| A61B 5/00 | (2006.01) |
| A61H 1/00 | (2006.01) |
| G06F 19/00 | (2011.01) |
| G06F 3/01 | (2006.01) |
| A61B 5/024 | (2006.01) |

(52) U.S. Cl.
CPC .......... *G06F 19/3406* (2013.01); *A61B 5/486* (2013.01); *A61B 5/7455* (2013.01); *G06F 3/016* (2013.01); *A61B 5/02438* (2013.01)

(58) Field of Classification Search
CPC .. A61B 5/02438; A61B 5/486; G06F 19/3406
See application file for complete search history.

(56) References Cited

U.S. PATENT DOCUMENTS

| | | | | |
|---|---|---|---|---|
| 5,348,008 | A | * | 9/1994 | Bornn et al. .................. 600/301 |
| 5,792,047 | A | * | 8/1998 | Coggins ......................... 600/300 |
| 5,967,975 | A | | 10/1999 | Ridgeway |
| 5,974,262 | A | * | 10/1999 | Fuller et al. ...................... 710/18 |
| 6,238,354 | B1 | * | 5/2001 | Alvarez ......................... 600/549 |
| 6,270,467 | B1 | * | 8/2001 | Yee .................................. 601/37 |
| 6,282,441 | B1 | | 8/2001 | Raymond et al. |
| 6,292,687 | B1 | * | 9/2001 | Lowell et al. ................. 600/515 |
| 6,309,342 | B1 | * | 10/2001 | Blazey et al. ................... 600/26 |
| 6,398,727 | B1 | * | 6/2002 | Bui et al. ...................... 600/300 |
| 6,406,426 | B1 | * | 6/2002 | Reuss et al. .................. 600/300 |
| 6,510,380 | B1 | * | 1/2003 | Curatolo et al. .............. 701/468 |

(Continued)

FOREIGN PATENT DOCUMENTS

| | | |
|---|---|---|
| JP | 10-295652 A | 11/1998 |
| JP | 2000-197670 | 7/2000 |

(Continued)

OTHER PUBLICATIONS

International Search Report and Written Opinion—PCT/US2008/057178.

(Continued)

*Primary Examiner* — Christopher A Flory
*Assistant Examiner* — Amanda Steinberg
(74) *Attorney, Agent, or Firm* — Miles & Stockbridge P.C.

(57) ABSTRACT

A haptic health feedback monitor includes a health parameter monitor that detects a health parameter. A haptic feedback generator receives the health parameter and compares it to a predetermined level. If the health parameter reaches or exceeds the level, a type of haptic feedback to generate is determined. The type of feedback may depend on which predetermined level is reached or exceeded. The haptic feedback generator then generates the determined type of haptic feedback.

34 Claims, 3 Drawing Sheets

(56) References Cited

U.S. PATENT DOCUMENTS

| | | | |
|---|---|---|---|
| 6,542,081 B2 * | 4/2003 | Torch | 340/575 |
| 6,553,244 B2 * | 4/2003 | Lesho et al. | 600/347 |
| 7,034,677 B2 * | 4/2006 | Steinthal et al. | 340/539.12 |
| 7,128,577 B2 * | 10/2006 | Renaud | 434/236 |
| 7,156,808 B2 | 1/2007 | Quy | |
| 7,525,426 B2 * | 4/2009 | Edelstein et al. | 340/539.13 |
| 7,905,832 B1 * | 3/2011 | Lau et al. | 600/300 |
| 8,007,436 B2 * | 8/2011 | Katayama | 600/301 |
| 2002/0078204 A1 * | 6/2002 | Newell et al. | 709/225 |
| 2002/0120188 A1 | 8/2002 | Brock et al. | |
| 2002/0145538 A1 * | 10/2002 | Bocko et al. | 340/870.28 |
| 2003/0036714 A1 | 2/2003 | Kuth | |
| 2003/0149344 A1 * | 8/2003 | Nizan | 600/300 |
| 2003/0163088 A1 * | 8/2003 | Blomquist | 604/131 |
| 2004/0070509 A1 * | 4/2004 | Grace et al. | 340/575 |
| 2004/0087839 A1 * | 5/2004 | Raymond et al. | 600/300 |
| 2004/0090318 A1 * | 5/2004 | Rothkop et al. | 340/435 |
| 2004/0122701 A1 * | 6/2004 | Dahlin et al. | 705/2 |
| 2005/0030166 A1 | 2/2005 | Kraus et al. | |
| 2005/0074732 A1 | 4/2005 | Morris | |
| 2005/0113653 A1 * | 5/2005 | Fox et al. | 600/300 |
| 2005/0124851 A1 * | 6/2005 | Patton et al. | 600/26 |
| 2005/0132290 A1 * | 6/2005 | Buchner et al. | 715/702 |
| 2005/0283053 A1 * | 12/2005 | deCharms | 600/300 |
| 2006/0010090 A1 * | 1/2006 | Brockway et al. | 706/46 |
| 2006/0015254 A1 * | 1/2006 | Smith | 702/3 |
| 2006/0122474 A1 * | 6/2006 | Teller et al. | 600/300 |
| 2006/0200051 A1 * | 9/2006 | Zandian et al. | 600/595 |
| 2006/0224046 A1 * | 10/2006 | Ramadas et al. | 600/300 |
| 2006/0284839 A1 | 12/2006 | Breed et al. | |
| 2006/0288137 A1 * | 12/2006 | Grant et al. | 710/62 |
| 2007/0018812 A1 * | 1/2007 | Allen et al. | 340/539.13 |
| 2007/0027369 A1 * | 2/2007 | Pagnacco et al. | 600/301 |
| 2007/0124027 A1 | 5/2007 | Betzitza et al. | |
| 2007/0191697 A1 * | 8/2007 | Lynn et al. | 600/323 |
| 2007/0232880 A1 * | 10/2007 | Siddiqui et al. | 600/368 |
| 2007/0280429 A1 * | 12/2007 | Binning | 379/37 |
| 2008/0139910 A1 * | 6/2008 | Mastrototaro et al. | 600/365 |
| 2008/0147004 A1 * | 6/2008 | Mann et al. | 604/131 |
| 2008/0177152 A1 * | 7/2008 | Donofrio et al. | 600/300 |
| 2008/0200774 A1 * | 8/2008 | Luo | 600/301 |
| 2008/0214903 A1 * | 9/2008 | Orbach | 600/301 |

FOREIGN PATENT DOCUMENTS

| | | |
|---|---|---|
| JP | 2003-146107 | 5/2003 |
| JP | 2007-506166 A | 3/2007 |
| WO | WO 2006/090371 A2 | 8/2006 |

OTHER PUBLICATIONS

Smart Heart, Heart Rate Monitor with Vibration Alert and Tap on Lens, User Manual.

Decision of Rejection as issued for Japanese Patent Application No. 2010-513284, dated Feb. 25, 2014.

Reexamination Report as issued in Japanese Patent Application No. 2010-513284, dated Nov. 11, 2014.

* cited by examiner

HAPTIC HEALTH FEEDBACK MONITORING

FIELD OF THE INVENTION

One embodiment of the present invention is directed to a haptic feedback system. More particularly, one embodiment of the present invention is directed to a system that generates haptic feedback based on monitored health parameters.

BACKGROUND INFORMATION

In the medical profession today, the advent of high technology has provided a myriad of impressive diagnostic tools. However the focus of this medical technology has been on diagnosis of acute conditions, rather than advanced warnings and preventive advice. Routine "checkups" are the recognized method of monitoring a person's health. Such examinations provide a physician with information relating to the patient's condition. However, unless a patient's checkup is fortuitously scheduled for a time at which symptoms of an ensuing illness are just developing, the checkup may not be effective in helping to detect the onset of an adverse medical condition.

Portable health monitors have been developed in the past which monitor body/health parameters specific to a particular medical condition. In some cases these monitors record specific parameter data, while in others they provide an output to the patient which is indicative of the physical parameters they sense. Some monitors simply provide an alarm when the parameters reach a pre-set level of particular concern. Others such as portable heart rate monitors provide a digital display of heart rate to the patient. Still others record heart rate over time. Patients use such heart rate monitors to warn them of high heart rates. Athletes use them to ensure that their physical training includes periods of elevated heart rate thought to be sufficient to promote conditioning. Similar monitors also exist for measuring other parameters.

Known methods of alerting users of health parameters are fairly limited. In many instances, a user needs to be alerted or informed of parameters without having to look at a specific display or listen for a distinctive noise. Based on the foregoing, there is a need for an improved system and method for monitoring and alerting a user of health parameters.

SUMMARY OF THE INVENTION

One embodiment is a haptic health feedback monitor that includes a health parameter monitor that detects a health parameter. A haptic feedback generator receives the health parameter and compares it to a predetermined level. If the health parameter reaches or exceeds the level, a type of haptic feedback to generate is determined. The type of feedback may depend on which predetermined level is reached or exceeded. The haptic feedback generator then generates the determined type of haptic feedback.

DETAILED DESCRIPTION

Embodiments of the present invention may include kinesthetic feedback (such as active and resistive force feedback) and/or tactile feedback (such as vibration, texture, and heat), more generally known collectively as "haptic feedback", to provide health parameters to a user. Haptic feedback can provide cues that enhance and simplify the user interface. Specifically, vibration effects, or vibrotactile haptic effects, may be useful in providing cues to users of electronic devices to alert the user to specific events, or provide realistic feedback to create greater sensory immersion within a simulated or virtual environment. One embodiment is a health monitoring system in which haptic feedback is used to alert a user of health parameter levels.

Figure 1:
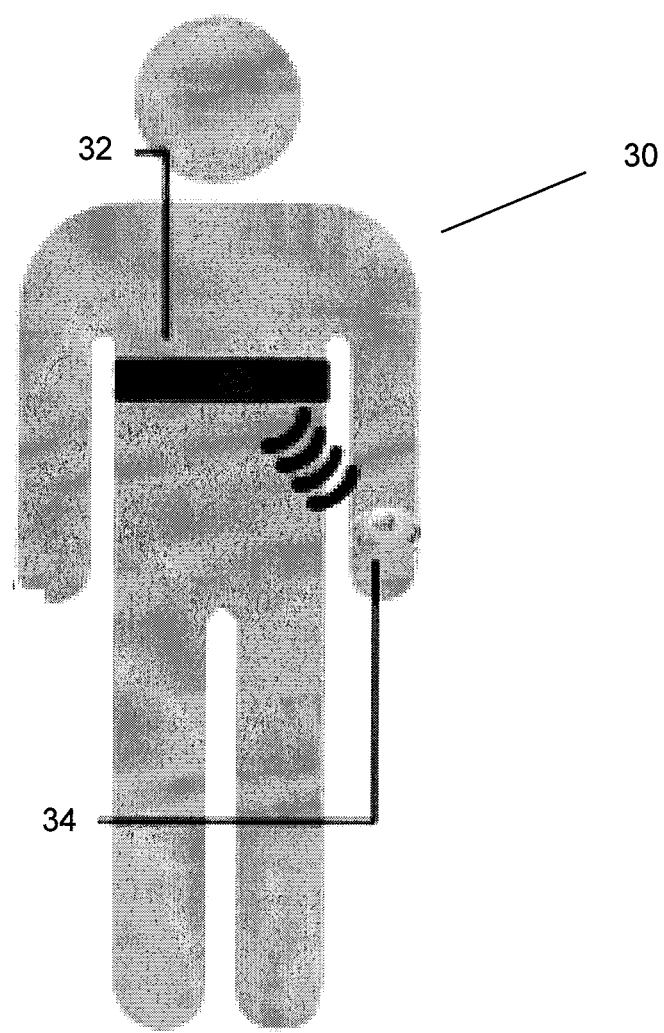
FIG. 1 is a plan view of a health monitoring system in accordance with one embodiment that monitors health parameters of a user.

FIG. 1 is a plan view of a health monitoring system 30 in accordance with one embodiment that monitors health parameters of a user. The system includes a health parameter monitor 32 coupled to a haptic feedback generator 34. Health parameter monitor 32 may be any type of device for monitoring health parameters. For example, embodiments that are used for disease management may monitor blood glucose, blood pressure, ambulatory ECG, respiratory, temperature, heart rate, blood salinity, blood electrolytes, hormones, blood iron, blood alcohol, etc. Embodiments that are used for healthy lifestyle management may include monitoring for temperature, heart rate, blood pressure, amount of work or rate of work performed, etc.

One embodiment of haptic parameter monitor 32 may be a chest strap, as shown in FIG. 1, that includes a variety of parametric sensors that can detect health parameters non-invasively. Other embodiments may detect health parameters in a more invasive method such as through sampling of blood or other body fluids. Health parameter monitor 32 may include a processor and memory.

In one embodiment, haptic feedback generator 34 is any type of device that is capable of communicating with health parameter monitor 32 to receive measured health parameters, and is capable of applying haptic feedback to a user in response to the health parameters. Haptic feedback generator 34 may be worn on the user's wrist, as shown in FIG. 1, or on any other portion of the user's body, including as a glove on a hand, a belt around the waist, a shoe or clothing or accessories such as a shirt, pants, undergarments, sunglasses, ear-pieces, rings, bracelets, necklaces, etc. Haptic feedback generator 34 may also be a device that is not "attached" to the user's body but still is able to apply haptic feedback that can be detected by the user. For example, a cellular telephone that can be slipped in the user's pocket may be used to apply a haptic feedback to the user. Further, haptic feedback generator 34 may be housed in the same physical device as health parameter monitor 32.

Figure 2:
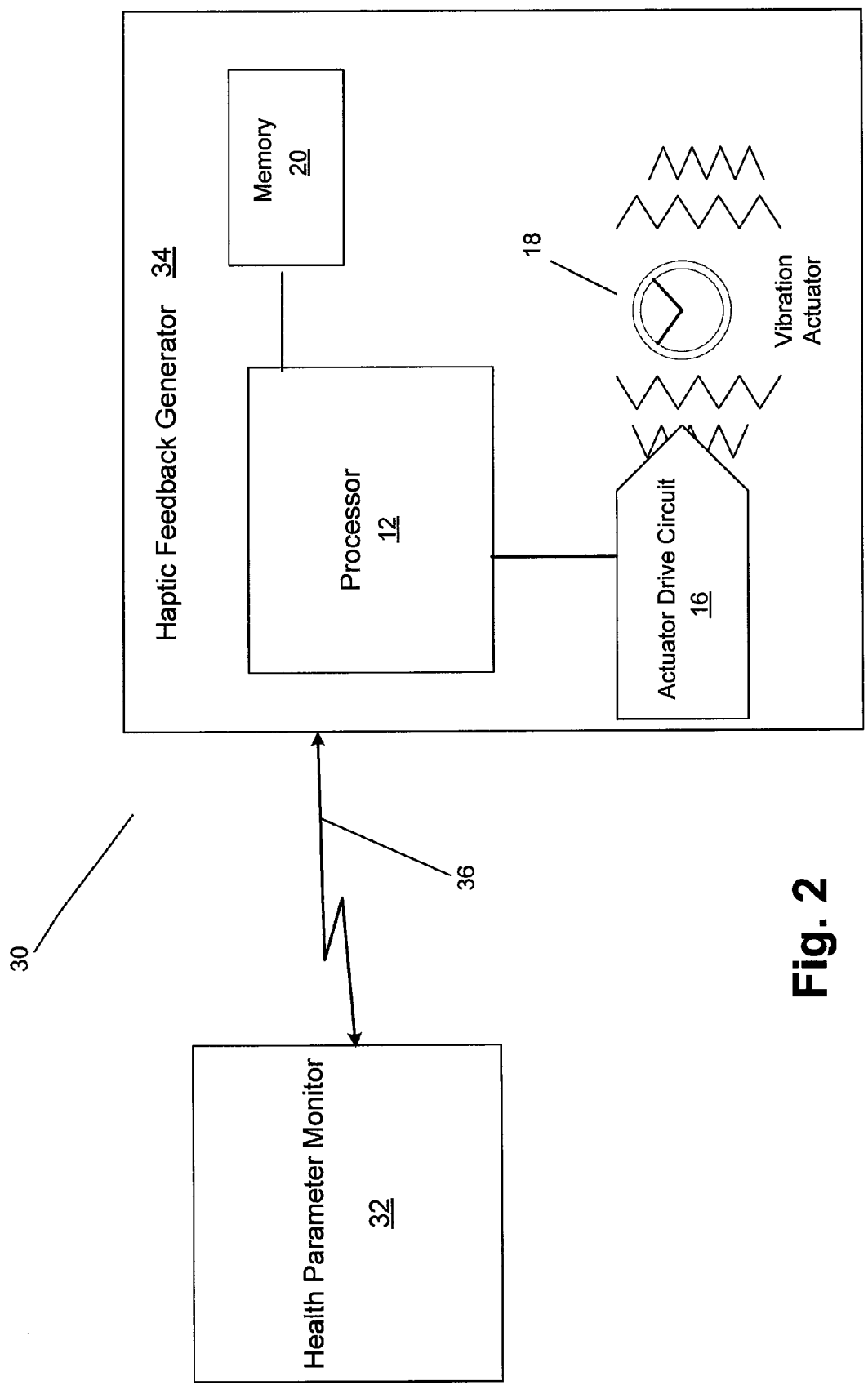
FIG. 2 is a block diagram of the health monitoring system in accordance with one embodiment.

FIG. 2 is a block diagram of health monitoring system 30 in accordance with one embodiment. Health parameter monitor 32 is in communications with haptic feedback generator 34 via communication link 36. Communication link may be any type of interface for communicating data, including wired, wireless, radio, infra-red ("IR"), etc. Health parameter monitor 32 and haptic feedback generator 34 include communication modules (not shown) for facilitating data communications via communication link 36.

Processor 12 can decide what haptic effects are to be played and the order in which the effects are played based on high level parameters which are based on information from the monitor 32 regarding health parameter values falling outside of or reaching predefined levels. In general, the high level parameters that define a particular haptic effect include magnitude, frequency, duration, attack level, attack time, fade level and fade time. These high level parameters can also be dynamically changed. Individual haptic effects can also be grouped together to form more complex haptic effects or timelines.

Processor 12 outputs the control signals to drive circuit 16 which includes electronic components and circuitry used to supply actuator 18 with the required electrical current and voltage to cause the desired haptic effects. Actuator 18 is a haptic device that generates a vibration on the body of haptic feedback generator 34 or in some other area so that it can be felt by the user. Actuator 18 may be, for example, an electromagnetic actuator such as an Eccentric Rotating Mass ("ERM") in which an eccentric mass is moved by a motor, a Linear Resonant Actuator ("LRA") in which a mass attached to a spring is driven back and forth, or a "smart material" such as piezoelectric, electro-active polymers or shape memory alloys.

Memory 20 can be any type of storage device, such as random access memory ("RAM") or read-only memory ("ROM"). Memory 20 stores instructions executed by processor 12. Memory 20 may also be located internal to processor 12, or any combination of internal and external memory. Memory 20 further stores data of measured parameters from haptic parameter monitor 32 so that it can be used at a later time.

Haptic feedback generator 34 can generate multiple types of haptic effects to communicate different information to the user. For example, for vibration based haptic effects, high amplitude, high frequency vibration can communicate one type of information, while low amplitude, low frequency vibration can communicate another type of information. Similarly, for temperature based haptic effects, a cold temperature or hot temperature may communicate two or more types of information. Other examples of possible haptic effects that can be varied to communicate more than one type of information include humidity levels (e.g., wet or dry) or the rigidity of generator 34 (e.g., it can be changed from loose and floppy to tight/constricting and rigid). All permutations and combinations of the various types of haptic feedback can be combined in embodiments to create compelling haptic effects. The use of varying patterns of haptic effects can also be used to communicate different information to the user. A limitless number of haptic patterns could be used to communicate a plethora of health-related information by varying not only the individual haptic effect amplitude, frequency and duration parameters, but by varying the durations between these haptic effects and by combining the same or dissimilar haptic effects into unique patterns for the purpose of this communication. For example, in one embodiment the application of a series of short duration haptic effects repeated at a set interval can communicate one type of information and the application of a series of long duration haptic effects at a different interval can communicate another type of information.

Many health parameters monitored by health parameter monitor 32 have various levels that may be of interest to a user. For example, for a measured heart rate a user might desire a haptic feedback when the heart rate exceeds a predetermined level (e.g., 180 beats per minute ("bpm")). However, some athletes attempt to get their heart rate within various "zones" such as Zone 1 (50-60% of maximum heart rate); Zone 2 (60-70% of maximum heart rate); Zone 3 (70-80% of maximum heart rate); Zone 4 (80-90% of maximum heart rate); Zone 5 (90-100% of maximum heart rate). For these users, it is beneficial to receive a different type of haptic effect when entering each zone. Similarly, one level of blood glucose may generate one type of haptic effect, while a second level, which may indicate that medication or other steps must be undertaken immediately, may generate another type of haptic effect.

Figure 3:
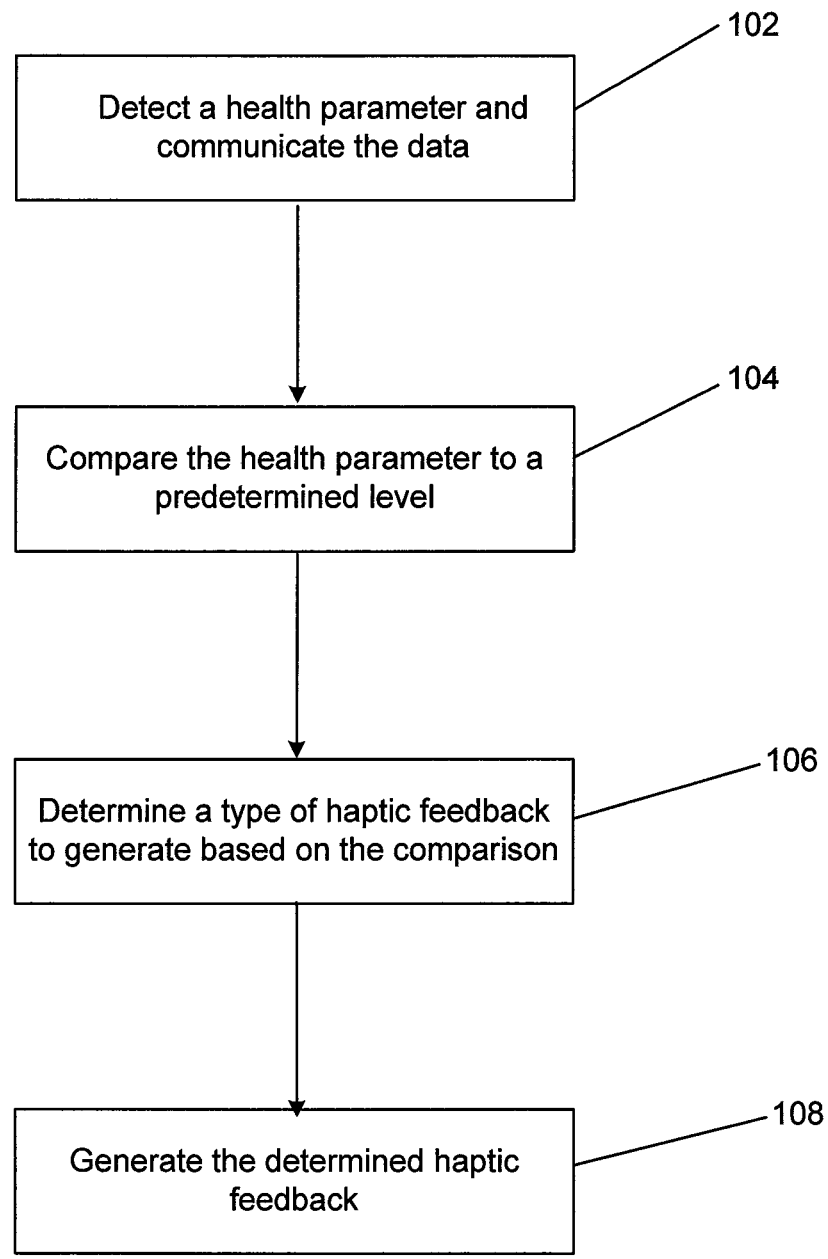
FIG. 3 is a flow diagram of the functionality of the health monitoring system in accordance with one embodiment.

FIG. 3 is a flow diagram of the functionality of health monitoring system 30 in accordance with one embodiment. In one embodiment, the functionality of the flow diagram of FIG. 3 is implemented by software stored in or loaded into memory and executed by a processor. In other embodiments, the functionality can be performed by hardware, or any combination of hardware and software. Further, any of the functionally may be performed by either monitor 32 or generator 34.

At 102, health parameter monitor 32 detects a health parameter and communicates that data to haptic feedback generator 34.

At 104, haptic feedback generator 34 compares the health parameter to a predetermined level, such as zone 2 heart rate, mildly high blood glucose level, etc.

At 106, based on the comparison, generator 34 determines a type of haptic feedback to generate.

At 108, the haptic feedback parameters are compiled and sent to the haptic device (e.g., actuator drive circuit 16 and vibration actuator 18) to create the haptic feedback. Therefore, the particular haptic feedback that is generated will depend on the type determined at 106. Similarly, different levels at 104 will result in a different type of haptic feedback being generated at 108.

In addition to generating haptic feedback at 108 to provide an alert to the user, in some embodiments the haptic feedback itself may counteract the health parameter. For example, if the type of haptic feedback is temperature based, a rising temperature can be counteracted by the application of a cold temperature haptic effect. or moisture released in response to the body suffering from arid conditions.

Further, the haptic feedback alert can be generated remotely from health parameter monitor 32 and can be applied to a user other than the user wearing health parameter monitor 32. For example, in combat situations, medics could be informed of a soldier's need for medical attention or more generally alerted to the need for medical attention for a group of soldiers based on an average of the group's vital stats readings. Further, those who care for the elderly or the physically disabled can be alerted for the need for medical attention or other type of assistance, or it can be used to remotely monitor children.

In one embodiment, health parameter monitor 32 further includes a Global Positioning System ("GPS") that generates information regarding the geographic location of the user. In one embodiment, the GPS information can be used after the alert has been triggered to assist in guiding medical or monitoring personal to the person needing attention. In one embodiment, after triggering a haptic health alert and communicating vital health information to the monitoring staff, the system can enter a GPS mode that provides guidance through a series of haptic effects of increasing amplitude, frequency, duration or patterns that assist in pinpointing the location of the person needing attention. In one embodiment, the haptic effects, in addition to being generated at a remote user, can also be used as a two-way communication system in sending one or more haptic effects to the injured person, letting them know a number of relevant facts such as: the alert has been sent; the alert has been received; help is on the way; GPS pinpointing has been activated; or the relative position or distance of medical assistance.

Several embodiments are specifically illustrated and/or described herein. However, it will be appreciated that modifications and variations of the present invention are covered by the above teachings and within the purview of the appended claims without departing from the spirit and intended scope of the invention.

What is claimed is:

1. A method of monitoring health of a person comprising:
   detecting a first health parameter and a second health parameter of the person with a health parameter monitor;
   comparing the first health parameter to a first predetermined level;
   determining a first type of haptic feedback to generate based on the comparing the first health parameter to the first predetermined level,
   the first type of haptic feedback being vibrotactile haptic feedback,
   the vibrotactile haptic feedback having a plurality of parameters,
   the plurality of parameters including a magnitude parameter, a frequency parameter, and a duration parameter, and
   at least one of the plurality of parameters varying based on the comparing the first health parameter to the first predetermined level;
   generating a first haptic effect, based on the first type of haptic feedback, for a user with a first haptic feedback generator, the user being different from the person with the health parameter monitor;
   comparing the second health parameter to a second predetermined level;
   determining a second type of haptic feedback to generate based on the comparing the second health parameter to the second predetermined level;
   generating a second haptic effect, based on the second type of haptic feedback, with the first haptic feedback generator; and
   guiding the user to the person after the generating the first haptic effect by providing a series of haptic effects to assist in pinpointing a location of the person.

2. The method of claim 1, wherein the first health parameter is at least one of heart rate, blood pressure, blood glucose level, respiratory level, temperature, blood alcohol level, blood iron level, blood salinity, blood electrolyte level or hormone level.

3. The method of claim 1, further comprising:
   generating the first haptic effect for the person with a second haptic feedback generator.

4. The method of claim 1, further comprising:
   transmitting a signal that indicates the location of the person with the health parameter monitor.

5. A haptic health feedback monitor comprising:
   a health parameter monitor that detects a first health parameter and a second health parameter of a person; and
   a haptic feedback generator coupled to the health parameter monitor,
   the haptic feedback generator including a processor that performs the operations of
   receiving the first health parameter,
   performing a comparison of the first health parameter to a first predetermined level,
   determining a first type of haptic feedback based on the comparison of the first health parameter to the first predetermined level,
   generating a first haptic effect, based on the first type of haptic feedback, to a user different from the person,
   receiving the second health parameter,
   performing a comparison of the second health parameter to a second predetermined level,
   determining a second type of haptic feedback based on the comparison of the second health parameter to the second predetermined level,
   generating a second haptic effect, based on the second type of haptic feedback, to the user, and
   guiding the user to the person after the first haptic effect is generated by providing a series of haptic effects to assist in pinpointing a location of the person,
   the first type of haptic feedback being vibrotactile haptic feedback,
   the vibrotactile haptic feedback having a plurality of parameters,
   the plurality of parameters including a magnitude parameter, a frequency parameter, and a duration parameter, and
   at least one of the plurality of parameters varying based on the comparison of the first health parameter to the first predetermined level.

6. The haptic health feedback monitor of claim 5, wherein the first health parameter is at least one of heart rate, blood pressure, blood glucose level, respiratory level, temperature, blood alcohol level, blood iron level, blood salinity, blood electrolyte level or hormone level.

7. The haptic health feedback monitor of claim 5, further comprising:
   a location determiner that determines a location of the health parameter monitor.

8. A non-transitory computer readable medium having instructions stored thereon that, when executed by a processor, cause the processor to perform the operations of:
   receiving a first health parameter of a person;
   comparing the first health parameter to a first predetermined level;
   determining a first type of haptic feedback based on the comparing the first health parameter to the first predetermined level,
   the first type of haptic feedback being vibrotactile haptic feedback,
   the vibrotactile haptic feedback having a plurality of parameters,
   the plurality of parameters including a magnitude parameter, a frequency parameter, and a duration parameter, and
   at least one of the plurality of parameters varying based on the comparing the first health parameter to the first predetermined level;
   generating a first haptic effect, based on the first type of haptic feedback, for a user who is different from the person;
   receiving a second health parameter;
   comparing the second health parameter to a second predetermined level;
   determining a second type of haptic feedback to generate based on the comparing the second health parameter to the second predetermined level;
   generating a second haptic effect, based the second type of haptic feedback, for the user; and guiding the user to the person after the generating the first haptic effect by providing a series of haptic effects to assist in pinpointing a location of the person.

9. The method of claim 4, further comprising:
receiving one or more third haptic effects for the person indicating a distance of the user from the person based on the location of the person.

10. The method of claim 1, further comprising:
receiving one or more third haptic effects for the person indicating that the first haptic effect has been communicated to the user.

11. The method of claim 10, wherein the indicating that the first haptic effect has been communicated to the user comprises at least one of: (i) indicating that the first haptic effect has been sent to the user, (ii) indicating that the first haptic effect has been received by the user, (iii) indicating that help is on the way, (iv) indicating that a global positioning system has been activated, and (v) indicating a relative position or a distance of the user.

12. The non-transitory computer readable medium of claim 8, wherein the first health parameter is at least one of heart rate, blood pressure, blood glucose level, respiratory level, temperature, blood alcohol level, blood iron level, blood salinity, blood electrolyte level or hormone level.

13. The non-transitory computer readable medium of claim 8, wherein the processor is further configured to perform the operation of generating the first haptic effect for the person.

14. The non-transitory computer readable medium of claim 8, wherein the processor is further configured to perform the operation of transmitting a signal that indicates the location of the person.

15. The method of claim 1,
wherein the first type of haptic feedback is different than the second type of haptic feedback,
the at least one of the plurality of parameters varies based on a respective one of the comparing the first health parameter to the first predetermined level or the comparing the second health parameter to the second predetermined level, and
the generating the first haptic effect includes combining the first type of haptic feedback with the second type of haptic feedback.

16. The haptic health feedback monitor of claim 5, wherein
the first type of haptic feedback is different than the second type of haptic feedback,
the at least one of the plurality of parameters varies based on a respective one of the comparison of the first health parameter to the first predetermined level or the comparison of the second health parameter to the second predetermined level, and
the haptic feedback generator is configured to generate the first haptic effect by combining the first type of haptic feedback with the second type of haptic feedback.

17. The non-transitory computer readable medium of claim 8, wherein
the first type of haptic feedback is different than the second type of haptic feedback,
the at least one of the plurality of parameters varies based on a respective one of the comparing the first health parameter to the first predetermined level or the comparing the second health parameter to the second predetermined level, and
the generating the first haptic effect includes combining the first type of haptic feedback with the second type of haptic feedback.

18. A method of monitoring health of a person comprising:
detecting a first health parameter and a second health parameter of the person with a health parameter monitor;
comparing the first health parameter to a first predetermined level;
determining a first type of haptic feedback to generate based on the comparing the first health parameter to the first predetermined level,
the first type of haptic feedback being vibrotactile haptic feedback,
the vibrotactile haptic feedback having a plurality of parameters, and
the plurality of parameters including a magnitude parameter, a frequency parameter, and a duration parameter;
detecting a second health parameter of the person with the health parameter monitor;
comparing the second health parameter to a second predetermined level;
determining a second type of haptic feedback to generate based on the comparing the second health parameter to the second predetermined level;
generating a first haptic effect, by combining the first type of haptic feedback with the second type of haptic feedback, for a user with a first haptic feedback generator, the user being different from the person with the health parameter monitor; and
guiding the user to the person after the generating the first haptic effect by providing a series of haptic effects to assist in pinpointing a location of the person,
wherein the first type of haptic feedback is different than the second type of haptic feedback, and
at least one of the plurality of parameters varies based on a respective one of the comparing the first health parameter to the first predetermined level or the comparing the second health parameter to the second predetermined level.

19. The method of claim 18, further comprising:
generating a third haptic effect, based on the second type of haptic feedback, with the first haptic feedback generator.

20. The method of claim 18, wherein the first health parameter is at least one of heart rate, blood pressure, blood glucose level, respiratory level, temperature, blood alcohol level, blood iron level, blood salinity, blood electrolyte level or hormone level.

21. The method of claim 18, further comprising:
generating the first haptic effect for the person with a second haptic feedback generator.

22. The method of claim 18, further comprising:
transmitting a signal that indicates the location of the person with the health parameter monitor.

23. The method of claim 22, further comprising:
receiving one or more third haptic effects for the person indicating a distance of the user from the person based on the location of the person.

24. The method of claim 18, further comprising:
receiving one or more third haptic effects for the person indicating that the first haptic effect has been communicated to the user.

25. The method of claim 24, wherein the indicating that the first haptic effect has been communicated to the user comprises at least one of: (i) indicating that the first haptic effect has been sent to the user, (ii) indicating that the first haptic effect has been received by the user, (iii) indicating that help is on the way, (iv) indicating that a global positioning system has been activated, and (v) indicating a relative position or a distance of the user.

26. A haptic health feedback monitor comprising:

a health parameter monitor that detects a first health parameter and a second health parameter of a person; and a haptic feedback generator coupled to the health parameter monitor, the haptic feedback generator including a processor that performs the operations of receiving the first health parameter, performing a comparison of the first health parameter to a first predetermined level, determining a first type of haptic feedback based on the comparison of the first health parameter to the first predetermined level, receiving the second health parameter, performing a comparison of the second health parameter to a second predetermined level, determining a second type of haptic feedback based on the comparison of the second health parameter to the second predetermined level, generating a first haptic effect, by combining the first type of haptic feedback with the second type of haptic feedback, to a user different from the person, and guiding the user to the person after the first haptic effect is generated by providing a series of haptic effects to assist in pinpointing a location of the person, the first type of haptic feedback being vibrotactile haptic feedback, the vibrotactile haptic feedback having a plurality of parameters, the plurality of parameters including a magnitude parameter, a frequency parameter, and a duration parameter, at least one of the plurality of parameters varying based on a respective one of the comparison of the first health parameter to the first predetermined level or the comparison of the second health parameter to the second predetermined level, and the first type of haptic feedback being different than the second type of haptic feedback.

27. The haptic health feedback monitor of claim 25, wherein the processor further performs the operation of:

generating a third haptic effect, based on the second type of haptic feedback, to the user.

28. The haptic health feedback monitor of claim 26, wherein the first health parameter is at least one of heart rate, blood pressure, blood glucose level, respiratory level, temperature, blood alcohol level, blood iron level, blood salinity, blood electrolyte level or hormone level.

29. The haptic health feedback monitor of claim 26, further comprising:

a location determiner that determines a location of the health parameter monitor.

30. A non-transitory computer readable medium having instructions stored thereon that, when executed by a processor, cause the processor to perform the operations of:

receiving a first health parameter of a person;

comparing the first health parameter to a first predetermined level;

determining a first type of haptic feedback based on the comparing the first health parameter to the first predetermined level, the first type of haptic feedback being vibrotactile haptic feedback, the vibrotactile haptic feedback having a plurality of parameters, and the plurality of parameters including a magnitude parameter, a frequency parameter, and a duration parameter;

receiving a second health parameter;

comparing the second health parameter to a second predetermined level;

determining a second type of haptic feedback based on the comparing the second health parameter to the second predetermined level;

generating a first haptic effect, by combining the first type of haptic feedback and the second type of haptic feedback, for a user who is different from the person; and guiding the user to the person after the generating the first haptic effect by providing a series of haptic effects to assist in pinpointing a location of the person, the first type of haptic feedback being different than the second type of haptic feedback, and at least one of the plurality of parameters varying based on a respective one of the comparing the first health parameter to the first predetermined level or the comparing the second health parameter to the second predetermined level.

31. The non-transitory computer readable medium of claim 30, wherein said processor further performs the operation of:

generating a third haptic effect, based the second type of haptic feedback, for the user.

32. The non-transitory computer readable medium of claim 30, wherein the first health parameter is at least one of heart rate, blood pressure, blood glucose level, respiratory level, temperature, blood alcohol level, blood iron level, blood salinity, blood electrolyte level or hormone level.

33. The non-transitory computer readable medium of claim 30, wherein the processor is further configured to perform the operation of generating the first haptic effect for the person.

34. The non-transitory computer readable medium of claim 30, wherein the processor is further configured to perform the operation of transmitting a signal that indicates the location of the person.

* * * * *